United States Patent [19]

McCall et al.

[11] Patent Number: 4,560,767

[45] Date of Patent: Dec. 24, 1985

[54] N-(2-AMINO-CYCLOALKENYL)BENZENEACETAMIDE AND -BENZAMIDE ANALGESICS AND TRITIATED KAPPA AGONISTS THEREFROM

[75] Inventors: John M. McCall, Kalamazoo; Robert A. Lahti, Galesburg, both of Mich.

[73] Assignee: The Upjohn Company, Kalamazoo, Mich.

[21] Appl. No.: 505,527

[22] Filed: Jun. 17, 1983

[51] Int. Cl.[4] .................. C07D 205/04; C07D 207/08; C07D 207/20; C07D 241/04

[52] U.S. Cl. ........................... 548/578; 260/239 A; 260/349; 260/465 D; 544/400; 548/515; 548/541; 548/543; 548/551; 548/565

[58] Field of Search ................ 514/429, 412, 424; 548/578, 565, 541, 515, 543, 551; 544/400; 260/239 AR

[56] References Cited

U.S. PATENT DOCUMENTS

| | | | |
|---|---|---|---|
| 4,065,573 | 12/1977 | Lednicer | 424/275 X |
| 4,098,904 | 7/1978 | Szmuszkovicz | 424/324 |
| 4,145,435 | 3/1979 | Szmuszkovicz | 424/274 |
| 4,148,914 | 4/1979 | Szmuszkovicz | 424/304 |
| 4,152,459 | 5/1979 | Szmuszkovicz | 424/324 |
| 4,153,717 | 5/1979 | Szmuszkovicz | 424/285 X |
| 4,179,501 | 12/1979 | Szmuszkovicz | 424/226 |
| 4,192,885 | 3/1980 | Szmuszkovicz | 424/285 X |
| 4,197,308 | 4/1980 | Szmuszkovicz | 424/244 X |
| 4,212,878 | 7/1980 | Lednicer et al. | 424/244 X |
| 4,215,114 | 7/1980 | Szmuszkovicz | 424/285 X |
| 4,438,130 | 3/1984 | Kaplan | 424/274 |

OTHER PUBLICATIONS

*Life Sciences*, 31, 2257–2260 (1982), "Properties . . . , U–50,488" by Robert A. Lahti et al.

*The J. of Pharmacology and Experimental Therapeutics*, 224, No. 1, 7–12 (1983), "U–50,488 . . . Agonist," by P. F. VonVoigtlander et al.

Primary Examiner—Joseph Paul Brust
Attorney, Agent, or Firm—John T. Reynolds

[57] ABSTRACT

Amino-cycloalkenyl-amide compounds, e.g., (1α,6β)-(±)-3,4-dichloro-N-methyl-N-(6-(1-pyrrolidinyl)-3-cyclohexen-1-yl)benzeneacetamide, and tritiated derivatives thereof, are useful as analgesics and as radio labeled compounds for pharmacological and metabolism studies in animals.

15 Claims, No Drawings

N-(2-AMINO-CYCLOALKENYL)BENZENEACETAMIDE AND -BENZAMIDE ANALGESICS AND TRITIATED KAPPA AGONISTS THEREFROM

INTRODUCTION

This invention relates to cycloalkenyl diamine derivative analgesics, which are related to other prior patented cycloalkyl diamine derivative analgesics, and to tritiated N-(2-aminocycloalkyl)benzeneacetamide and -benzamide compounds which are useful as radio labeled compounds for kappa receptors, in studies of types of analgesia induced by the compounds, and in metabolism studies to learn the metabolic fate of their non-tritiated analog compounds which are intended as the active analgesic drug compounds.

BACKGROUND OF THE INVENTION

Cycloaliphatic ring saturated diamine derivative analgesic compounds are described in Szmuszkovicz U.S. Pat. No. 4,145,435 and U.S. Pat. No. 4,098,904. Studies on selected members of the above described patented compounds continue. For example, trans-2-(3,4-dichlorophenyl)-N-methyl-N-[2-(1-pyrrolidinyl)-cyclohexyl]acetamide, in its pharmaceutically acceptable salt form, has been found by the pharmacologists to be a highly selective kappa type analgesic agonist. Efforts to learn more about how the analgesic activity of these known compounds work has led to the need to prepare new compounds, described herein, which could be used, either as analgesics per se, or as chemical intermediates to prepare tritiated derivatives of now prior patented or published cycloalkane diamine derivative analgesic compounds.

OBJECTS OF THE INVENTION

It is an object of this invention to provide a class of new cycloalkenyl diamine derivative compounds which are useful per se as analgesic compounds, or which are useful as chemical intermediates for making the corresponding tritiated cycloalkyl diamine derivative compounds, which are useful as radio labeled compounds for use in studies of the types and effects of various analgesic compounds.

It is another object of this invention to provide a class of tritiated cycloalkane diamine derivative compounds, and a method for preparing these tritiated cycloalkane diamine derivative compounds in a manner so that the resulting tritiated compound will be stable for use, that is, it will not decompose substantially, so as to be essentially useless in subsequent pharmacological and metabolic studies.

Other objects, aspects and advantages of this invention will be apparent to those skilled in the art from the description and claims which follow.

SUMMARY OF THE INVENTION

Briefly, this invention provides some new 2-amino-cycloalkenylamide compounds, described in detail below, e.g., (1α,6β)-(−)-3,4-dichloro-N-methyl-N-(6-(1-pyrrolidinyl)-3-cyclohexen-1-yl)benzeneacetamide, and the salts thereof, which are useful as analgesics, or as chemical intermediates to make the corresponding tritiated or hydrogenated 2-amino-cycloalkyl-amide compounds therefrom. This invention also provides the tritiated compounds per se, e.g., 3,4-dichloro-N-methyl-N-[2-(1-pyrrolidinyl)cyclohexyl-4,5-$t_2$]benzeneacetamide and salts thereof and a method for making these tritiated compounds in radio-stable form so they can be used as radio labeled compounds for phamacological or metabolism studies.

DETAILED DESCRIPTION OF THE INVENTION

One aspect of this invention provides new 2-amino-cycloalkenylamide compounds of formula (I) wherein p and n are the integers 1 or 2 so that the resulting cycloalkenyl ring has from 6 to 8 ring carbons;

the wavy line (∼) bond between the 6-(or 7- or 8-)position ring carbon atom and the nitrogen indicates that the bond can be either cis- or trans- with respect to the 1-substituent of the cycloalkenyl ring;

q is 0 or 1;

E is oxygen or bivalent sulfur;

X and Y are independently selected from the group consisting of hydrogen, a halogen having an atomic number of from 9 to 35; trifluoromethyl, nitro, $C_1$ to $C_3$-alkyloxy, hydroxy, azido, $C_1$ to $C_3$-alkyl, phenyl, methanesulfonyl, cyano, amino, $C_1$ to $C_3$-alkoxycarbonyl, $C_1$ to $C_3$-alkanoyloxy, $C_1$ to $C_3$-carboxacylamino (—NHC(O)$R_4$), sulfonic acid (—SO$_3$H), $C_1$ to $C_3$-alkanoyl, ($C_2$ to $C_5$-alkenyl)—CH$_2$—O— and benzoyl;

R is hydrogen or $C_1$ to $C_3$-alkyl;

$R_1$ and $R_2$, taken separately, are hydrogen or $C_1$ to $C_3$-alkyl; or when $R_1$ is hydrogen or $C_1$ to $C_3$-alkyl, $R_2$ is $C_1$ to $C_6$-alkyl, —CH$_2$CF$_3$, CH$_2$—($C_2$ to $C_5$-alkenyl), —CH$_2$—(hydroxy($C_1$ to $C_4$-alkyl)), $C_3$ to $C_6$-cycloalkyl, ($C_3$ to $C_4$-cycloalkyl)—CH$_2$, phenyl-($C_1$ to $C_3$-alkyl)-; or $R_1$ and $R_2$, taken together with the nitrogen to which they are bonded complete (a) a 1-azetidinyl or 1-pyrrolidinyl ring further unsubstituted or substituted in the 3-position of the ring with hydroxy, $C_1$ to $C_3$-alkyl, $C_1$ to $C_3$-alkyloxy or $C_1$ to $C_3$-alkanoyloxy;

(b) a 1-piperazinyl ring, further unsubstituted or substituted on the 4-position nitrogen with a $C_1$ to $C_3$-alkyl;

(c) a 2,5-dihydro-1H-pyrrol-1-yl ring of the formula

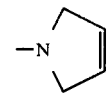

(d) a 3-azabicyclo[3.1.0]hexan-3-yl ring of the formula

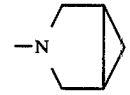

(e) a 3-azabicyclo[3.2.0]heptan-3-yl ring of the formula

$R_4$ is hydrogen or $C_1$ to $C_2$-alkyl, and the acid addition salts thereof, particularly the pharmaceutically acceptable salts thereof.

A preferred sub-group of the formula I compounds of this invention are those where p and n are each 1, so that the resulting cycloalkenyl ring has 6 carbon atoms, the substituent on the 6-position is trans with respect to the 1-substituent of the cycloalkenyl ring, R is $C_1$ to $C_3$-alkyl, $R_1$ and $R_2$, taken separately are $C_1$ to $C_3$-alkyl, or $R_1$ and $R_2$ taken together with the nitrogen to which they are bonded complete a 1-pyrrolidinyl or a 2,5-dihydro-1H-pyrrol-1-yl ring, E is oxygen, q is 0 or 1, and at least one of X and Y is a halogen having an atomic number of from 9 to 35, in the 3- or 4-positions of the phenyl ring, and pharmacologically acceptable salts thereof.

Examples of such compounds include the cis and trans isomers of:

3,4-dichloro-N-methyl-N-[6-(1-pyrrolidinyl)-3-cyclohexen-1-yl]benzeneacetamide;

4-Bromo-N-methyl-N-[6-(dimethylamino)-3-cyclohexen-1-yl]benzamide;

3,4-Dichloro-N-ethyl-N-[6-(diethylamino)-3-cyclohexen-1-yl]benzeneacetamide;

4-Fluoro-N-(n-propyl)-N-[6-(1-piperazinyl)-3-cyclohexen-1-yl]benzeneacetamide;

4-Bromo-N-methyl-N-[6-(3-azabicyclo[3.1.0]hexan-3-yl)-3-cyclohexen-1-yl]benzeneacetamide;

3,4-Difluoro-N-methyl-N-[6-(1-pyrrolidinyl)-3-cyclohexen-1-yl]benzamide;

3,4-Dibromo-N-methyl-N-[6-(4-methyl-1-piperazinyl)-3-cyclohexen-1-yl]benzeneacetamide, and the like and the pharmacologically acceptable salts thereof.

The compounds of formula I in their free base or acid addition salt forms, in their crystalline state may sometimes be isolated as solvates, i.e., mixed with a discrete quantity of solvent, e.g., water, ethyl acetate, ethyl ether, methanol, methylene chloride, N,N-dimethylformamide (DMF), dimethylsulfoxide (DMSO), or the like, associated physically, and thus not affecting the chemical entity per se. It will also be understood that some acid addition salt forms, e.g., oxalic acid salt, and the like, might be used to assist extracting the desired amino-cycloalkenyl-amide product (I) from its reaction mixture, and such salt forms might also be useful as chemical intermediates for making the tritiated aminocycloalkyl-amide products (VI) described hereinbelow. But, if the selected above described amino-cycloalkenyl-amide compound (I) is to be used, per se, as an analgesic drug, the selected acid for salt formation will be pharmaceutically acceptable, that is, the selected acid salt will be selected on the basis of a variety of concerns by people involved with, e.g., chemical stability, pharmacological acceptability, dissolution properties, flow properties, storage, and handleability in high speed manufacture equipment, and the like.

It will be recognized by those skilled in the organic chemical art that the carbon atoms at positions 1 and 6 of 6-membered ring or 1 and 7 of 7-membered ring or 1 and 8 of 8-membered ring cycloalkenyl compounds of structure (I), or at positions 1 and 2 of a compound of structure (VI), to which nitrogens are bonded are asymmetrically substituted. Each of these two carbon atoms can independently possess an R or S- configuration and thus for example a compound of the formula (I) may have as many as $2^2$ or 4 stereoisomers which comprise two pairs of enantiomers; each enantiomeric pair is termed a racemate. See, for example, J. B. Hendrickson, D. J. Cram, and G. S. Hammond, Organic Chemistry, Third Edition, McGraw-Hill Book Company, New York, N.Y., 1970, pages 198–230, particularly pages 207, 208, 213, 215. Of the two racemates, one will have the nitrogen-containing groups at positions 1 and 6 of structure (I) in a trans orientation: that is, the groups will be on opposite sides of the plane of the cycloalkenyl ring; such compounds are sometimes generally referred to in this specification as trans compounds. The other racemate will have the nitrogen-containing groups at positions 1 and 6 of structure (I) in a cis orientation: that is, the groups will be on the same side of the cycloalkenyl ring; such compounds are sometimes generally referred to in this specification as cis compounds. The two racemates of structure (I) or structure (VI) compounds can each exist as a mixture of the two enantiomers or each enantiomer of each pair can be separated. Varying mixtures of enantiomers are also possible. When it is desired to specify for a structure (I) or structure (VI) compound the configuration of the other asymmetric center relative to that of position 1, this is done according to the Chemical Abstracts Service publication, "Naming and Indexing of Chemical Substances for CHEMICAL ABSTRACTS during the Ninth Collective Period (1972–1976)," a reprint of Section IV (Selection of Index Names for Chemical Substances) from the CHEMICAL ABSTRACTS Volume 76 Index Guide. Accordingly, the relative stereochemistry of two asymmetric carbon atoms in the cycloalkenyl ring of formula I compounds is indicated by: (1) the arbitrary designation of 1α for the orientation of the substituent on (asymmetric) carbon atom number one; (2) the designation Xα or Xβ when the substituent on (asymmetric) carbon atom number X is on the same or opposite side of the plane of the cycloalkenyl ring, respectively, relative to said $C_1$ substituent.

Two isomers which differ only in the stereochemistry at one asymmetric carbon atom of the cycloaliphatic ring are sometimes referred to herein as epimers.

If desired the formula I compounds of this invention can be resolved into their respective d- and l-optical isomers by methods known in the art. In this case, the optical resolution can be done by at least two different routes. The resolving agents by either route are any of the known resolving agents such as optically active camphorsulfonic acid, bis-p-toluoyltartaric acid, tartaric acid, diacetyl tartaric acid and the like, which are commercially available and which are commonly used for resolution of amines (bases), as for example in Organic Synthesis, Coll. Vol. V., p. 932 (1973), resolution of R-(+) and S-(−)-α-phenylethylamine with (−)-tartaric acid.

By the first method for resolving the compounds of this invention, for example, one of the aminoamide compounds can be converted into its optically active diastereomeric salts by reaction with an optically active acid—examples mentioned above—in a manner standard in the isomer resolution art. These diastereomeric salts can then be separated by conventional means such as differential crystallization. Diastereomeric salts have different crystallization properties, which are taken advantage of in this separation. On neutralization of each diastereomeric salt with aqueous base the corresponding optically active enantiomers of the free amino amide can be obtained, each of which can subsequently and separately be converted as hereinafter described in the examples to the desired acid addition salt.

By the second method, which in the case of some of these compounds is preferred, the formula I compounds can be made into their respective d- and l-isomers, by first resolving each cis- or trans-1,2-cycloaliphatic unsymmetrically substituted amino-alcohol or diamine into its respective d- or l-isomers by treatment with the resolving agent, crystallization, separation and regeneration of the respective d- and l-compounds, for example, trans-d-diamine, trans-l-diamine, or the cis-d-diamine and cis-l-diamine, and then reacting the respective resolved diamine starting material with the desired aracyl imidazole (III), the acyl halide (IV) or the acid (V) in the presence of a condensing agent to form the respective cis or trans-d- or l-compound of formula I, which can then be converted to any desired pharmaceutically acceptable acid addition salt by procedures exemplified hereinafter.

In the above formula I or formula VI compounds, the halogens having atomic numbers cf from 9 to 35 are fluorine, chlorine and bromine, the term "$C_1$ to $C_3$-alkyl" means methyl, ethyl, n-propyl and isopropyl. $C_1$ to $C_2$-alkyl means methyl or ethyl. $C_1$ to $C_4$-alkyl further includes the butyl group and its isomeric forms, e.g., n-butyl, isobutyl, tert-butyl, and the like. $C_1$ to $C_6$-alkyl further includes butyl, pentyl and hexyl groups in their isomeric forms, e.g., n-butyl, isobutyl, tert-butyl, n-pentyl, neopentyl, tert-pentyl, n-hexyl, isohexyl, tert-hexyl, and the like. The term $-CH_2-(C_2$ to $C_5$-alkenyl) means propenyl, butenyl, pentenyl and hexenyl groups in which the carbon to carbon double bond is no closer than the Beta carbon atom from the atom to which the group is bonded. The simplest example is the allyl group. $C_3$ to $C_4$-cycloalkyl means cyclopropyl and cyclobutyl; $C_3$ to $C_6$-cycloalkyl means cyclopropyl, cyclobutyl, cyclopentyl and cyclohexyl.

Acid addition salts can be prepared by reacting a formula I free base with a stoichiometric amount of an acid, such as hydrogen chloride, hydrogen bromide, hydrogen iodide, sulfuric acid, phosphoric acid, acetic acid, lactic acid, citric acid, succinic acid, benzoic acid, salicyclic acid, pamoic acid, cyclohexanesulfamic acid, methanesulfonic, naphthalenesulfonic, p-toluenesulfonic, maleic, fumaric, oxalic acids and the like. The reaction can be carried out in aqueous or organic liquid solvent or non-aqueous media such as diethyl ether, ethyl acetate, methanol and the like. Non-aqueous media are preferred. When it is desired to obtain optically resolved products in crystalline form, it may be more convenient to form salts such as maleates, citrates or pamoates rather than the inorganic acid addition salts, such as the hydrochlorides. Also, whereas oxalic acid and other equivalent acids can be used to produce the amino-amide product in a more easily handled solid form, e.g., in plant manufacturing isolation procedures, it would preferably not be used as a pharmaceutically acceptable salt form of the amino-amide product.

We have discovered that these above formula I amino-cycloalkenylamide compounds are useful as the preferred precursor compounds, for use as chemical intermediates to make tritiated derivatives thereof (VI) which are useful as radio-labeled compounds in pharmacology, analgesic and metabolic studies. The forms of these formula I compounds with the S absolute configuration at both asymmetric carbon atoms also have potent analgesic activity in standard laboratory animal tests.

It has been found for representative formula I compounds, having the $(1\alpha,6\beta)$-3,4-dichloro-N-methyl-N-[6-(1-pyrrolidinyl)-3-cyclohexen-1-yl]benzeneacetamide structure that the (−)-enantiomer, that is the enantiomer with the (1S,6S) absolute configuration, has potent analgesic activity in standard laboratory animal tests. Analgesic activity in these same tests has not been demonstrated for the (+)-enantiomer, that is the enantiomer with the (1R,6R) absolute configuration. However in vitro site selective binding studies have shown that the (1R,6R)-enantiomer does bind to the kappa receptor. The absolute configuration of the (1S,6S)-enantiomer was established by hydrogenation thereof to the known $(1\alpha,2\beta)$-(−)-3,4-dichloro-N-methyl-N-[1-pyrrolidinyl)cyclohexyl]benzeneacetamide, which is known to have the (1S,2S) configuration and which can also be named as trans-(−)-2-(3,4-dichlorophenyl)-N-methyl-N-[2-(1-pyrrolidinyl)cyclohexyl]acetamide as in Example 35 of Szmuszkovicz, U.S. Pat. No. 4,145,435. The information presently available does not allow the conclusion that the other enantiomers of this invention with the R absolute configuration at both asymmetric carbon atoms would be inactive when tested at up to about 75 mg/kg in the standard laboratory analgesic tests. In general however the enantiomers, the racemates, and mixtures of enantiomers containing substantial amounts of the enantiomer of compounds of this invention having the S configuration at both asymmetric carbon atoms are preferred both for analgesic purposes and for use as intermediates to prepare tritiated compounds as described herein for pharmacological, analgesic, and metabolic studies.

However, the enantiomers with the R absolute configuration at both asymmetric carbon atoms, included herein which do not show analgesic activity in the standard analgesic laboratory animal tests are useful in pharmacological and metabolic studies to compare the pharmacological and metabolic results obtained therewith against the results obtained in the pharmacological and metabolic testing of the corresponding enantiomers with the S absolute configuration at both asymmetric carbon atoms to more fully learn and understand the causes for the analgesic, other pharmacological effects and metabolic fate of the analgesically active enantiomers of the defined compounds.

In general, the new compounds of this invention (formula I compounds above) can be prepared by reacting the selected 1,2-cycloaliphatic diamine of the formula II, wherein p, n, R, $R_1$, and $R_2$, are as defined above with a suitable acyl source such as: (1) the appropriate acyl imidazole of the formula III wherein q, E, X and Y are as defined above; (2) or with an acyl halide of the formula IV, wherein M is chloride or bromide and q, E, X and Y are as defined above in the presence of an acid scavenger such as triethylamine; or (3) with the carboxylic acid of the formula V, in the presence of a condensing agent, such as a carbodiimide, wherein q, E, X and Y are as defined above, in an organic solvent for the reactants, preferably in a chlorinated alkane, e.g., methylene chloride, ethylene dichloride, chloroform or carbon tetrachloride or in an ether solvent such as diethyl ether, or a cyclic ether solvent such as tetrahydrofuran (THF) or dioxane, or the like, until the compound of this invention is produced. Carbodiimides such as dicyclohexylcarbodiimide or diisopropylcarbodiimide can be used as condensing agents.

The reactants (II) and (III) or (II) and (IV) or (II) and (V) can be mixed in substantially equimolar proportions to effect formation of the desired product (I), but in cases where the non-pertinent amino nitrogens are protected against reaction, if one of the reactants (II), (III), (IV) and (V) is more expensive than the other, it is sometimes preferred to use a stoichiometric excess of the less expensive reactant to insure that substantially all of the more expensive reactant is consumed in the reactions. The reaction will proceed at ambient temperature for most combinations of reactants, but for some combinations of reactants, variations from the initial to final reaction conditions may vary between $-25°$ C. and reflux temperature of the mixture depending on the reactivity of the reactants, the desired reaction time, the solvent being used, the molar proportions, and similar factors of concern to the chemist operating the process.

Procedures for preparing the aracyl imidazoles (III) and acyl halide (IV) reactants used to form compounds of this invention are known in the art. See, for example, R. B. Wagner and H. D. Zook, SYNTHETIC ORGANIC CHEMISTRY, 1953, John Wiley and Sons, Chapter 17, p. 546 et seq. The aracyl imidazole can be prepared in situ by reacting carbonyldiimidazole with the acid of the formula (V) in an organic solvent. The carboxylic acids (V) are either known in the art or are prepared by methods known in the art.

The preferred process for making or preparing the trans aminocycloalkenyl amides of this invention, and optionally the hydrogenated or tritiated derivatives therefrom is shown by the attached Process Flow Sheet I. The following comments are offered.

1. The oxidation [O] of the cycloalkadiene (XX) can be conducted by adding dropwise a solution of approximately a molar equivalent amount of a peracid, for example m-chloroperbenzoic acid or 40% peracetic acid additionally containing a small amount of an alkali metal buffering salt such as sodium acetate, to a solution of the 6 to 8 ring carbon cycloalkadiene and when the 40% peracetic acid is used, some anhydrous alkali metal carbonate such as sodium carbonate, in an organic solvent such as a $C_1$ to $C_2$-halogenated alkane, e.g., methylene chloride, ethylene dichloride, chloroform, carbon tetrachloride or other solvent for the cycloalkadiene while cooling the mixture to control the speed of the reaction. The mixture can be stirred or otherwise agitated to effect good mixing action. When addition is complete the mixture can be allowed to warm to room temperature, while stirring, and cooled again. The mixture is stirred until a negative starch iodide paper test is obtained. The cycloalkenyl epoxide (XXI) is recovered as a residue from the organic solvent, after filtration, by distillation of the solvent.

2. The cycloepoxide (XXI) can be reacted with the selected 2-amino group compound (XXII) in a water mixture for a time sufficient to open the epoxide ring and to form the selected racemic 2-amino cycloalkenol (XXIII) (one enantiomer is illustrated), which can be recovered from the reaction mixture by partitioning the reaction mixture into aqueous and organic solvent phases. The organic solvent phase takes up the aminoalcohol compound (XXIII) therein. The organic phase can be dried, the solvent removed, to leave as residue the intermediate product XXIII.

3. The amino alcohol (XXIII) can be converted to the cycloalkenyl-1,2-diamine (II, e.g., XXIV) (one enantiomer is illustrated) by dissolving the amino-alcohol (XXIII) in an organic solvent therefor, e.g., methylene chloride, adding a hydrogen halide scavenging base, e.g., triethylamine, dimethylaniline, pyridine, or the like, cooling the mixture to a temperature sufficient to control the speed of the reaction which follows, e.g., to about 0° C., and then treating the mixture with an alkanesulfonyl halide, e.g., methanesulfonyl chloride. The mixture is stirred for a time to ensure completion of the reaction. About 35 minutes is generally sufficient. Then the reaction mixture can be partitioned into liquid phases with ice water. The organic phase is separated, dried with a drying salt and concentrated. The residue can be placed in a pressure apparatus, treated with the selected $H_2N$—R amine in water or other appropriate diluent, and heated to effect reaction, e.g., to 70° to 100° C. for about 20 hours or so to form the $R_1R_2N$-cycloalkenyl-N-R-amine (XXIV) intermediate. This diamine intermediate can be recovered from its reaction mixture by liquid phase partition, aqueous acidic, basic and pH neutral washes of the organic phase, and concentration or distillation procedure.

It may be desirable or advantageous to reverse the order of addition of the amines $HN(R_1)R_2$ and $H_2N$—R, using nitrogen protecting groups as necessary as described hereinbelow, as described in U.S. Pat. Nos. 4,359,476 and 4,360,531. The amines $HN(R_1)R_2$ and $H_2N$—R are either known in the art or can be prepared by methods known in the art.

4. For the separation of the laevo ($-$) and dextro ($+$) stereo enantiomers of the diamine XXIV, the diamine product from step 3, above, is reacted with any appropriate diastereomer forming acid, e.g., with di-p-toluoyl-d-tartaric acid, by dissolving the diamine and the acid in separate portions of a common solvent such as methanol and then mixing the solutions. The solutions can be stirred to ensure complete mixing and then allowed to stand to form the crystalline salt. The salt is filtered, and recrystallized several times to improve its purity. The crystals can then be partitioned between an organic solvent such as methylene chloride and basic aqueous phases such as an aqueous alkali metal carbonate solution. The organic liquid phase, containing the dissolved free base salt, can be separated, dried and concentrated to a residue of one of the stereo ($+$) or ($-$) forms of the salt. The mother liquor can be concentrated, partitioned between an aqueous basic pH solution, e.g., a 10 percent sodium hydroxide solution and an organic solvent, e.g., ethyl acetate. The organic liquid phase, containing the dissolved stereo form free base, can be washed with aqueous solution such as an aqueous sodium chloride solution, dried and concentrated to leave as residue the other stereo isomer of the diamine.

5. The selected stereo-form ($+$) or ($-$) of the above diamine can then be acylated with the selected phenylacetic acid or benzoic acid side chain. For example, for making an analgesically active compound, XXVI, the selected substituted phenylacetic acid or benzoic acid can be dissolved in an organic solvent, e.g., methylene chloride, cooled and treated with an acylation activating agent such as carbonyldiimidazole to form an acylation-activated form of the selected acid. Then, the selected stereo form of the above diamine can be mixed therewith in at least molar equivalent amounts. To form the (1R,6R) form of the amino-cycloalkenyl-amide product [XXVI (1R,6R)] we use the (1R,6R) stereo form of the above diamine (XXVa). The reaction mixture is stirred for a time to ensure as complete reaction as desired, and then the reaction mixture is treated to separate the amino-cycloalkenyl-amide product [XXVI (1R,6R)] therefrom. If a crystalline salt form of the product is desired the product can be dissolved in an appropriate organic solvent, e.g., methanol, and treated with enough of the selected acid, e.g., maleic acid, to form the salt which crystallizes out, with concentration of the solvent volume, or the use of other organic solvent diluent (such as diethyl ether) or diluents if necessary.

By selection of the opposite stereo form (1S,6S) of the diamine (XXVb) for reaction with the selected acylating acid the corresponding (1S,6S) stereo form of the new amino-cycloalkenyl-amide product [XXVI (1S,6S)] can be made. Salts thereof can be made, as described above.

The cis compounds of formula I of this invention are synthesized from the cycloalkadiene (XX) by methods known in the art, for example, by methods disclosed in U.S. Pat. Nos. 4,359,476 and 4,360,531.

The cycloalkadiene starting materials XX are either known in the art or can be prepared by methods known in the art. In the synthesis of certain compounds of the formula I, for example, those comounds wherein one or both of $R_1$ and $R_2$ are hydrogen, the use of protecting groups may be desirable. The use of such protecting groups is known in the art and is described, for example, in U.S. Pat. Nos. 4,360,531 and 4,359,476. Throughout the synthesis of compounds of the formula I of this invention, care must be taken that the carbon-carbon double bond which ultimately becomes the carbon-carbon double bond of the cycloalkenyl ring of formula I compounds is not undesirably altered by reaction conditions used. It may be desirable to protect this carbon-carbon double bond during synthesis of formula I compounds by methods known in the art.

For a representative compound of this invention (see Example 1, Part E hereinbelow), it has been found that the dextro (+) form of the diamine XXV(b) is converted to the laevo (−) form of the amino-cycloalkenyl-amide of the formula XXVI. Both compounds XXV(b) and the resulting amino-cycloalkenyl-amide have the (1S,6S) absolute configuration.

Conversely the laevo (−) form of the diamine XXV(a) is converted to the dextro (+) form of the amino-cycloalkenyl-amide, both compounds having the (1R,6R) absolute configuration.

It has been discovered that the amino-cycloalkenyl-amide compounds of this invention, and particularly the enantiomers thereof with the S absolute configuration at both asymmetric carbon atoms, the racemates and mixtures containing substantial amounts of said enantiomer, are the preferred precursor compounds for making radio-stable, that is, decomposition resistant tritium-containing forms of saturated derivatives of these compounds by reaction with tritium.

This carbon double bond to single bond saturation reaction can be done, for example, by dissolving the selected amino-cycloalkenyl-amide free base (XXVI) in an organic solvent, e.g., ethyl acetate, adding an appropriate amount of hydrogenation or tritiation catalyst and then hydrogenating or mixing an at least molar equivalent preferably an excess amount of tritium therewith for a time sufficient to effect essentially complete saturation of the cycloalkenyl ring double bond and to form the product (XXVII) where each Z is hydrogen or tritium, depending upon which reactant, hydrogen or tritium, was used. It is generally believed that such a reaction with $Z_2$ wherein $Z_2$ is hydrogen or tritium proceeds to introduce two Z atoms in a cis relationship to each other. In a compound of the formula (VI) the Z atoms can be either cis or trans with respect to other substituents on the cycloaliphatic ring.

When the above ring saturation reaction with tritium is carried out on a representative compound of copending U.S. application, Szmuszkovicz et al., Ser. No. 06/495,857 filed May 18, 1983, namely on 1S-(1α,2β)-(−)-3,4-dichloro-N-[2-(2,5-dihydro-1H-pyrrol-1-yl)cyclohexyl]-N-methylbenzeneacetamide (Example 2 thereof), the resulting tritiated product apparently decomposes rather rapidly, so that as a practical matter such product is not very useful for further pharmacological or metabolic studies in animals.

The stable-form tritiated compounds of this invention have the structure (VI) wherein p and n are the integers 1 or 2 so that the resulting cycloalkenyl ring has from 6 to 8 ring carbons;

the wavy line (∼) bond between the 2-position cycloalkenyl ring carbon atom and the nitrogen indicates that the bond can be either cis or trans with respect to the 1-substituent of the cycloalkenyl ring; the Z groups can be cis or trans with respect to the other substituents on the cycloaliphatic ring;

each Z is tritium;

q is 0 or 1;

E is oxygen or bivalent sulfur;

X and Y are independently selected from the group consisting of hydrogen, a halogen having an atomic number of from 9 to 35; trifluoromethyl, $C_1$ to $C_3$-alkyloxy, hydroxy, $C_1$ to $C_3$-alkyl, phenyl, methanesulfonyl, amino, $C_1$ to $C_3$-alkoxycarbonyl, $C_1$ to $C_3$-alkanoyloxy, $C_1$ to $C_3$-carboxacylamino (—NH—C(O)R$_4$), sulfonic acid (—SO$_3$H), $C_1$ to $C_3$-alkanoyl, and benzoyl;

R is hydrogen or $C_1$ to $C_3$-alkyl;

$R_1$ and $R_2$, taken separately, are hydrogen or $C_1$ to $C_3$-alkyl; or when $R_1$ is hydrogen or $C_1$ to $C_3$-alkyl, $R_2$ is $C_1$ to $C_6$-alkyl, —CH$_2$CF$_3$, —CH$_2$—(hydroxy($C_1$ to $C_4$-alkyl)), $C_3$ to $C_6$-cycloalkyl, ($C_3$ to $C_4$-cycloalkyl)—CH$_2$—, phenyl-($C_1$ to $C_3$-alkyl)-, or $R_1$ and $R_2$, taken together with the nitrogen to which they are bonded complete:

(a) a 1-azetidinyl or 1-pyrrolidinyl ring further unsubstituted or substituted in the 3-position of the ring with hydroxy, $C_1$ to $C_3$-alkyl, $C_1$ to $C_3$-alkyloxy, or $C_1$ to $C_3$-alkanoyloxy;

(b) a 1-piperazinyl ring further unsubstituted or substituted on the 4-position nitrogen with a $C_1$ to $C_3$-alkyl;

(c) a 3-azabicyclo[3.1.0]hexan-3-yl ring of the formula

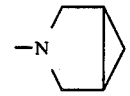

(d) a 3-azabicyclo[3.2.0]heptan-3-yl ring of the formula

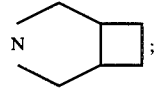

$R_4$ is hydrogen or $C_1$ to $C_2$-alkyl;

and the acid addition salts thereof, particularly the pharmaceutically acceptable salts thereof. Such stable form tritiated compounds are useful in identifying kappa receptor-mediated analgesic activity of test compounds, in studying kappa receptor-mediated analgesia, and in studying the role of kappa receptors in animals including humans. Such compounds are useful as test analgesic drugs for administration to valuable animals, in appropriate dosage amounts, to trace the physiological paths of travel of drug in the body, to trace its metabolic chemistry and mode of elimination from the body. Pharmacologists and metabolism chemists hope to learn from the studies answers to such questions as what greek-letter receptor type of analgesic action any particular test compound gives, how it works, how it travels in the body, and how it decomposes.

The amino-cycloalkenyl-amide compounds of the formula I, for example, [XXVI (1S,6S)] and [XXVI (1R,6R)] are useful as analgesic drugs, in their mixed ($\pm$) isomeric form, and particularly in the stereo form in which both asymmetric carbon atoms have the S absolute configuration, in reasonable dosage form amounts, as predicted by tests of representative compounds in standard laboratory animal tests such as the tail flick, tail pinch, screen climb and HCl writing tests, and these compounds have lower physical dependence liability than analgesics such as morphine and methadone.

This invention also includes the above compounds in pharmaceutical compositions as the active analgesic or pharmacological or metabolic study form of the drug. For use, these compositions are prepared into the appropriate dosage unit form for administration to the test animal, or valuable animal or human patient, as appropriate.

The term "dosage unit form" as used in this specification and in the claims refers to physically discrete units suitable as unitary dosages for mammalian subjects, each unit containing as the essential active ingredient a predetermined quantity of a compound of this invention with the required pharmaceutical means which adapt said ingredient for systemic administration. The specification for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals, these being features of the present invention. Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Capsules, both hard and soft, are filled with compositions of these amino-cycloalkenyl-amide active ingredients in combinations with suitable diluents and excipients, for example, edible oils, talc, calcium carbonate and the like and also calcium stearate. Liquid preparations for oral administration are prepared in water or aqueous vehicles which advantageously contain suspending agents, for example, methylcellulose, acacia, polyvinylpyrrolidone, polyvinyl alcohol and the like. In the case of injectable forms, the injectable formulation must be sterile and must be fluid to the extent that easy syringeability exists. Such preparations must be stable under the conditions of manufacture and storage, and ordinarily contain in addition to the basic solvent or suspending liquid, preservatives in the nature of bacteriostatic and fungistatic agents, for example, parabens, chlorobutanol, benzyl alcohol, phenol, thimerosal, and the like. In many cases, it is preferable to include osmotically active agents, for example, sugars or sodium chloride in isotonic concentrations. Carriers and vehicles include vegetable oils, ethanol, polyols, for example, glycerol, propylene glycol, liquid polyethylene glycol, and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 0.5 to about 350 mg of the essential active ingredient per dosage unit form, which as aforesaid may be in the form of a semi-solid or solid, oral or rectal preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain analgesic effects within the aforesaid effective non-toxic range or the amount needed to trace the metabolic travel and metabolic fate of the test compound in the body. Expressed otherwise, when used systemically, an amount of the essential active ingredient is provided to a recipient within a range from about 0.01 mg per kg to about 5 mg per kg of body weight of the recipient. Preferred dosages for most applications are 0.05 to 2.0 mg per kg of body weight.

The useful pharmaceutical dosage unit forms of these compounds in pharmaceutical formulations are preferably adapted for systemic administration to obtain analgesic effects comprising an effective, non-toxic amount of a compound according to formula I or as its pharmacologically acceptable salt.

Further, the invention relates to methods of obtaining analgesic effects in mammals, for example, humans and valuable warm-blooded animals such as dogs, cats, horses and other commercially valuable animals, by administering systemically to the mammals the aforesaid pharmaceutical dosage unit forms supplying an effective, non-toxic amount of the analgesic compounds for analgesic effects. These preferred compounds have an advantage, to a greater extent, depending upon the particular compound, of having lower physical dependence liability than known analgesic compounds such as morphine and methadone.

Representative examples of these formula I compounds have $ED_{50}$ values of less than about 75 mg/kg s.c. (subcutaneous administration) in standard laboratory animal analgesic tests such as the tail flick, pinch, and hydrochloric acid writhing tests, and the more potent of them have $ED_{50}$ values of less than 10 mg/kg (s.c.) or (p.o.) in these tests, while at the same time possessing low apparent physical dependence liability as compared to commercial analgesics used as standards. The procedures used to determine these properties are essentially those of Way et al., (Way, E. L. et al., "Simultaneous Quantitative Assessment of Morphine Tolerance and Physical Dependence", J. Pharmacol. Exp. Ther., 167, pp. 1–8 (1969)) and Saalens et al., (Saalens, J. K. et al., "The Mouse Jumping Test—A Simple Screening Method to Estimate the Physical Dependence Capacity of Analgesics", Arch. Int. Pharmacodyn., 190, pp. 213-218 (1971)). Statistical effective doses ($ED_{50}$ values) and 95% confidence limits were calculated by the method of Spearman and Karber (Finney, D. J., "Statistical Methods in Biological Assay", Hafner Publ., (1952)).

Known analgesic drugs such as morphine and methadone exhibit analgesic $ED_{50}$ values of less than 2 mg/kg s.c., respectively, in these standard analgesic tail flick, pinch and writhing tests, but are known to have high apparent physical dependence liability effects, and this is confirmed by their (morphine and methadone) having relatively low naloxone jumping $ED_{50}$ values ranging from 12 to 30 mg/kg s.c.

The compounds of this invention are also characterized by having only low to moderate apparent physical dependence liabiity, compared to standards such as morphine and methadone.

The invention is further exemplified by the following detailed examples, the procedures of which can be used to prepare compounds of this invention, but these examples are not intended to limit the scope of the invention. All temperatures are in degrees centigrade unless otherwise noted. For brevity, Hg means mercury, bp means boiling point, IR (or ir) means infrared spectrum points of reference, m/e means the mass of a mass spectral fragment divided by its charge, M+ means the mass corresponding to the parent molecular ion, $CH_2Cl_2$ means methylene chloride solvent, dried ($K_2CO_3$) or dried ($Na_2SO_4$) or dried ($MgSO_4$) means the organic layer was dried over anhydrous forms of potassium carbonate, sodium sulfate, or magnesium sulfate, respectively, mp means melting point, NMR (or nmr) means nuclear magnetic resonance spectrum and NMR ($CDCl_3$) means a nuclear magnetic resonance spectrum made using deuteriochloroform as a solvent and values in parts per million are reported as downfield shifts from a tetramethylsilane internal reference; DBN means 1,5-diazabicyclo[4.3.0]non-5-ene; h means hour(s), $N_2$ means nitrogen, tlc means thin layer chromatography procedures, HPLC means high pressure liquid chromatography procedures, $Na_2SO_3$ means sodium sulfite, $NaHCO_3$ means sodium bicarbonate, DMSO is dimethylsulfoxide, Skellysolve B (or Skelly B) is a tradename for a solvent of essentially n-hexane, bp 60°-68° C. (Merck Index, Ninth Edition (1976) page 1106), $Et_2O$ means diethyl ether, MeOH means methanol, THF means tetrahydrofuran, $H_2O$ means water, $CHCl_3$ means chloroform, brine is saturated aqueous sodium chloride solution, DMF means N,N-dimethylformamide, $Et_3N$ is triethyl-amine, HRMS means high resolution mass spectrum, EtOAc means ethyl acetate; HCl means hydrogen chloride.

All temperatures are in degrees Centigrade, unless otherwise noted. 5% Pd-C means 5% palladium on carbon hydrogenation catalyst (commercially available). The rotation in degrees is determined in methanol solution in a one decimeter path length cell at the temperature indicated (generally 25° C.). The specific rotation, $[\alpha]_D$ is calculated from the observed rotation.

EXAMPLE 1

(1α,6β)-(−)-3,4-Dichloro-N-methyl-N-[6-(1-pyrrolidinyl)-3-cyclohexen-1-yl]benzeneacetamide, and its (Z)-2-butene dioate (1:1)

A. 1,4-Cyclohexadiene Monoepoxide

A mixture of 25.0 g (0.312 mol) of 1,4-cyclohexadiene and 133 g of anhydrous sodium carbonate in 300 ml. of methylene chloride was cooled in ice and stirred mechanically. A solution of 0.5 g sodium acetate in 57 g of 40% peracetic acid was added dropwise. The solution was stirred, allowed to warm to room temperature and then cooled again. The mixture was stirred until a negative starch iodide paper test was obtained. The mixture was filtered. The organic layer was concentrated. The residue was distilled with house vacuum (down to about 25 mm Hg) at a bath temperature which increased from 50° to 90°. A yield of 17.95 g of 1,4-cyclohexadiene monoepoxide was obtained. The structure of this subtitled compound is supported by its nmr spectrum.

B. (1α,6β)-(±)-6-(1-Pyrrolidinyl)cyclohex-3-en-1-ol

The monoepoxide from Part A, above, thus obtained (17.95 g) was heated at 70° in 25 ml of water with 13.30 g of pyrrolidine for 24 hr. The reaction mixture was partitioned between methylene chloride and aqueous saturated sodium bicarbonate. The organic phase was dried over sodium sulfate and concentrated. The residue was distilled (110°-120° pot/0.4 mm Hg) to yield 26 g of the desired product, (1α,6β)-(±)-6-(1-pyrrolidinyl)cyclohex-3-en-1-ol. The structure of this subtitled compound is supported by its nmr spectrum.

C. (1α,6β)-(±)-N-Methyl-6-(1-pyrrolidinyl)cyclohex-3-en-1-amine

The 26 g of aminoalcohol thus obtained from Part B, above, was dissolved in 400 ml methylene chloride and 19 g of triethylamine, cooled to 0° and treated with 14 ml of methanesulfonyl chloride. The mixture was stirred for 35 min and then partitioned with ice water. The organic phase was dried over sodium sulfate and concentrated. The residue was heated at 70° in a 1 liter Parr bomb (pressure vessel) for 20 hr with 90 ml of 40% methylamine in water. The mixture was then partitioned between ether and water. The organic phase was washed with water again and then with 10% aqueous HCl. The acidic aqueous wash was made basic with 10% sodium hydroxide and then extracted three times with ether. The ether phase was extracted with brine, dried through sodium sulfate and concentrated. The residue was short path distilled (0.11 mm Hg/70° bath) to yield 8.70 g of (1α,6β)-(±)-N-methyl-6-(1-pyrrolidinyl)cyclohex-3-en-1-amine. The structure of this subtitled compound is supported by its nmr spectrum.

D. Resolution of (1α,6β)-(±)-N-methyl-6-(1-pyrrolidinyl)cyclohex-3-en-1-amine ((+) and (−) separated)

This amine from Part C, above, (8.70 g, 0.0488 mol) and 18.66 g (0.0483 mol) of di-p-toluoyl-d-tartaric acid were each dissolved in a minimum volume of methanol. The solutions were mixed. After standing, the crystals were filtered to yield a weight of 23.72 g. This material was recrystallized four more times from methanol. The crystals were then partitioned between methylene chloride and aqueous sodium carbonate. The organic phase was dried over sodium sulfate and then concentrated to yield 2.86 g of the (+) above-named product with $[\alpha]_D^{25}+91.2°$ (7.8 mg/ml in methanol). The mother liquors were concentrated and the residue was partitioned with 10% sodium hydroxide and ethyl acetate. The organic phase was washed with brine, dried over sodium sulfate and concentrated to yield 2.97 g of the (−) above-named amine.

E. (1α,6β)-(−)-3,4-Dichloro-N-methyl-N-[6-(1-pyrrolidinyl)-3-cyclohexen-1-yl]benzeneacetamide and its (Z)-2-butene dioate (1:1)

A solution of 4.23 g of 3,4-dichlorophenylacetic acid in 200 ml of methylene chloride was treated at 0° with 3.35 g of carbonyldiimidazole. The mixture was stirred for 40 min. Then, 2.86 g (0.0159 mol) of the (+) amine from the resolution which was previously described in Part D, above, was added. The mixture was stirred for 24 hr and partitioned with saturated aqueous sodium bicarbonate. The organic phase was dried and concentrated to yield 4.93 g of the named (−)-benzeneacetamide product which had an $[\alpha]_D^{25} -24°$ (6.75 mg/ml in methanol). The product was dissolved in a minimum volume of methanol and treated with 1.48 g of maleic acid which had been dissolved in a minimum volume of methanol and the mixture was diluted with diethyl ether. The resultant crystals were filtered to yield 5.02 g of the named salt product, mp 167°–169°, $[\alpha]_D^{25} -29.7°$ (10.0 mg/ml in methanol).

Anal. Calcd. for $C_{19}H_{24}Cl_2N_2O \cdot C_4H_4O_4$: C, 57.14; H, 5.84; N, 5.97. Found: C, 56.67; H, 5.75; N, 5.62.

EXAMPLE 2

(1α,6β)-(+)-3,4-Dichloro-N-methyl-N-[6-(1-pyrrolidinyl)-3-cyclohexen-1-yl]benzeneacetamide, and its (Z)-2-butene dioate (1:1)

In a similar manner, 4.40 g of 3,4-dichlorophenylacetic acid, 3.47 g of carbonyldiimidazole and 2.97 g of the (−) amine from Part D, above, were reacted to yield the above-named (+)-benzeneacetamide product. This product was chromatographed on silica gel (2% methanol (which was saturated with ammonia gas)/98% ethyl acetate) to yield 3.22 g of pure benzeneacetamide product, $[\alpha]_D^{25} +34°$ (8.2 mg/ml in methanol). This benzeneacetamide product was treated with 1.011 g of maleic acid in methanol and the mixture was diluted with diethyl ether to yield 3.56 g of the above named product salt, mp 174°–175° C., $[\alpha]_D^{25} +35.3°$ (10.0 mg/ml in methanol).

Anal. Calcd. for $C_{19}H_{24}Cl_2N_2O \cdot C_4H_4O_4$: C, 57.14; H, 5.84; N, 5.97. Found: C, 56.75; H, 5.92; N. 5.60

EXAMPLE 3

Hydrogenation of (1α,6β)-(+)-3,4-Dichloro-N-methyl-N-[6-(1-pyrrolidinyl)-3-cyclohexen-1-yl]benzeneacetamide, free base. Preparation of (1α,2β)-(+)-3,4-dichloro-N-methyl-N-[2-(1-pyrrolidinyl)cyclohexyl]benzeneacetamide and its maleate salt A mixture of 55 mg of the free base from Example 2 above and 10 mg of 5% Pd-C was hydrogenated at atmospheric pressure in 20 ml of ethyl acetate with vigorous stirring for 1.5 hr. The mixture was filtered through Celite ® filter aid and concentrated. The residue was chromatographed (20×20×0.1 cm prep silica gel plate eluted with 10% methanol (which was saturated with ammonia)/(90% ethyl acetate). The material recovered from the plate was partitioned between methylene chloride and aqueous sodium bicarbonate. The organic phase was dried over sodium sulfate and concentrated to yield 23.6 mg of the known (1α,2β)-(+)-3,4-dichloro-N-methyl-N-[2-(1-pyrrolidinyl)cyclohexyl]benzeneacetamide product, the compound of Example 34 of Szmuszkovicz, U.S. Pat. No. 4,145,435. This was converted to the maleic acid salt with 7.4 mg of maleic acid. A 29.0 mg/ml solution in methanol had $[\alpha]_D^{25}$ of +39°.

EXAMPLE 4

Hydrogenation of (1α,6β)-(−)-3,4-dichloro-N-methyl-N-[6-(1-pyrrolidinyl)-3-cyclohexen-1-yl]benzeneacetamide, free base. Preparation of (1α,2β)-(−)-3,4-dichloro-N-methyl-N-[2-(1-pyrrolidinyl)cyclohexyl]benzeneacetamide and its maleate salt Using the procedure of Example 3 above, a mixture of 55 mg of the titled cyclohexene compound from Example 1, Part E above, and 10 mg of 5% Pd-C was hydrogenated at atmospheric pressure in 20 ml of ethyl acetate to give the known (1α,2β)-(−)-3,4-dichloro-N-methyl-N-[2-(1-pyrrolidinyl)cyclohexyl]benzeneacetamide, maleate salt, specific rotation $[\alpha]_D^{25} -37.5°$ (19.2 mg/ml in methanol), the compound of Example 35 of Szmuszkovicz; U.S. Pat. No. 4,145,435.

EXAMPLE 5

Tritiation of (1α,6β)-(−)-3,4-dichloro-N-methyl-N-[6-(1-pyrrolidinyl)-3-cyclohexen-1-yl)benzeneacetamide. Preparation of (1α,2β)-(−)-3,4-dichloro-N-methyl-N-[2-(1-pyrrolidinyl)cyclohexyl-4,5-$t_2$]benzeneacetamide (the compound of the formula XXVII wherein R is methyl, E is oxygen, q is 1, X and Y together are 3,4-dichloro, $N(R_1)R_2$ is 1-pyrrolidinyl, and each Z is tritium)

This tritiation is conducted using the method of Example 3 above. The purification of the product subsequently described was also performed using the corresponding compound not containing tritium. A mixture of 50 mg of the titled cyclohexene compound prepared as in Example 1, Part E above, and 25 mg of 5% Pd-C catalyst in 15 ml of ethyl acetate is tritiated at atmospheric pressure with vigorous stirring for 16 hr, taking appropriate precautions to avoid exposure of the operator to hazardous levels of radioactivity. The catalyst is removed by filtration through Celite ® filter aid and excess tritium is removed by evaporation and dissolution of the residue in ethyl acetate. To avoid radiation exposure this ethyl acetate solution is further processed portionwise. A portion of this ethyl acetate solution is washed with saturated aqueous sodium bicarbonate solution. The aqueous phase is extracted three times with ethyl acetate. The combined product-containing ethyl acetate phases are dried (Na$_2$SO$_4$), and the solvent is evaporated. The resulting residue is dissolved in a small volume of water:ethanol (4:1) and placed on a C$_{18}$-Sep-Pak ® (Waters Associates) chromatography column which was previously washed with methanol and then water. The column is eluted with water:methanol in a step gradient starting with pure water and proceeding to pure methanol and taking 1 ml fractions. Fractions 16–19 are eluted with water:methanol 2:8 and then 0:10 and contain the desired tritiated product. These fractions are pooled and the solvent is evaporated. The resulting residue is dissolved in n-hexane and chromatographed on a 5 to 6 cm×0.5 cm column of neutral alumina (Woelm), which column was made up using n-hexane. The column is eluted with first hexane and then 10% and then 15% ethyl acetate in hexane, collecting 1 ml fractions. The desired product is contained in fractions 8 and 9 which are eluted with 15% ethyl acetate in hexane. These fractions are combined and the solvent is evaporated. The resulting residue is dissolved in water:ethanol (4:1) and chromatographed by HPLC on a $C_{18}$ reversed phase column eluting with a solvent consisting of 650 ml of acetonitrile, 350 ml of 0.1M aqueous sodium dihydrogen phosphate ($NaH_2PO_4$), 3 ml of triethylamine and 4 ml of phosphoric acid ($H_3PO_4$) to produce the purified tilted tritiated compound. An aliquot of this purified material is combined with the corresponding non-tritiated compound and upon chromatography by HPLC on a $C_{18}$ reversed phase column as described above in the final purification step, and using ultraviolet spectroscopy for detecting the unlabeled compound and scintillation counting for detecting the tritium-labeled compound, the labeled and unlabeled compounds are found to chromatograph together confirming the identity of the purified titled tritiated compound.

EXAMPLE 6

(1α,6β)-(±)-3,4-Dichloro-N-methyl-N-[6-(1-pyrrolidinyl-3-cyclohexen-1-yl]benzeneacetamide, and its (Z)-2-butene dioate (1:1)

A solution of 4.23 g of 3,4-dichlorophenylacetic acid in 200 ml of methylene chloride is treated at 0° C. with 3.35 g of carbonyldiimidazole. The mixture is stirred for 40 minutes. Then 2.86 g (0.0159 mole) of the (±)-amine from Example 1, Part C, above, is added. The mixture is stirred for 24 hr and partitioned with saturated aqueous sodium bicarbonate. The organic phase is dried and concentrated to yield the titled (±)-benzeneacetamide product free base which is dissolved in a minimum volume of methanol and treated with one equivalent of maleic acid which has been dissolved in a minimum volume of methanol and the mixture is diluted with diethyl ether to give the titled maleate salt, mp 152°–155° C.

EXAMPLE 7

(1α,6β)-(±)-N-Methyl-N-[6-(1-pyrrolidinyl)-3-cyclohexen-1-yl]benzeneacetamide and its maleate salt Using the method of Example 6, a solution of 2.81 g of phenylacetic acid in 200 ml of methylene chloride is treated at 0° C. with 3.35 g of carbonyldiimidazole. The mixture is stirred for 40 minutes. Then 2.86 g (0.0159 mole) of the (±)-amine from Example 1, Part C, above is added. The mixture is stirred for 24 hr and partitioned with saturated aqueous sodium bicarbonate. The organic phase is dried and concentrated to yield the titled (±)-benzeneacetamide product free base which is dissolved in a minimum volume of methanol and treated with one equivalent of maleic acid which has been dissolved in a minimum volume of methanol, and the mixture is diluted with diethyl ether to give the titled maleate salt.

EXAMPLE 8

(1α,6β)-(−)-N-Methyl-N-[6-(1-pyrrolidinyl)-3-cyclohexen-1-yl]benzeneacetamide and its maleate salt Using the procedure of Example 7 above but using instead of the (±)-amine 2.86 g of the (+)-amine prepared as described in Example 1, Part D above, the titled (−)-benzeneacetamide product is obtained and is further converted to its maleate salt. This product has the (1S,6S) absolute configuration.

EXAMPLE 9

(1α,6β)-(+)-N-Methyl-N-[6-(1-pyrrolidinyl)-3-cyclohexen-1-yl]benzeneacetamide

Using the procedure of Example 7 above but using instead of the (±)-amine 2.86 g of the (−)-amine prepared as described in Example 1, Part D above, the titled (+)-benzeneacetamide product is obtained and is further converted to its maleate salt. This product has the (1R,6R) absolute configuration.

EXAMPLE 10

Tritiation of (1α,6β)-(−)-N-Methyl-N-[6-(1-pyrrolidinyl)-3-cyclohexen-1-yl]benzeneacetamide. Preparation of (α,2β)-(−)-N-Methyl-N-[2-(1-pyrrolidinyl)cyclohexyl-4,5-$t_2$]benzeneacetamide (the compound of the formula XXVII wherein R is methyl, E is oxygen, q is 1, X and Y are each hydrogen, $N(R_1)R_2$ is 1-pyrrolidinyl and each Z is tritium)

Using the procedure of Example 5 above the titled cyclohexene compound prepared as in Example 8 above is tritiated and the product is purified to produce the purified titled tritiated compound.

GENERAL CHEMICAL STRUCTURES

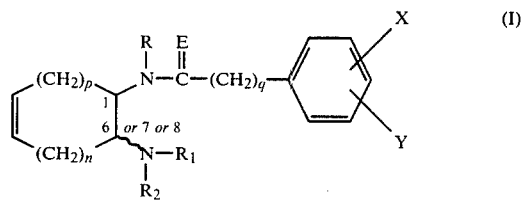
(I)

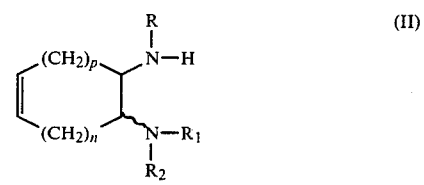
(II)

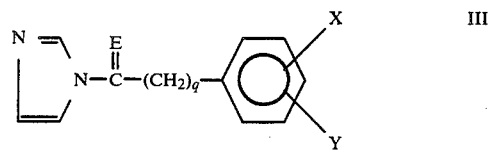
III

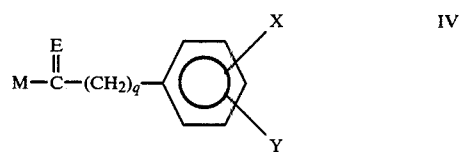
IV

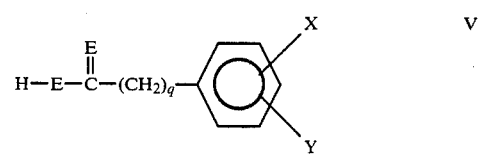
V

-continued
GENERAL CHEMICAL STRUCTURES
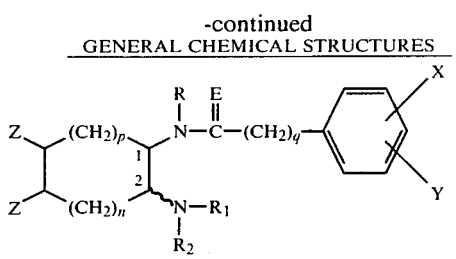
(VI)
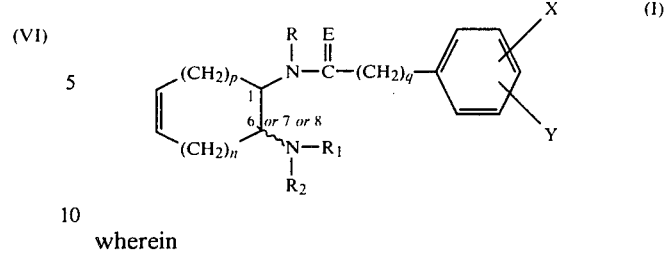
(I)
wherein
PROCESS FLOW SHEET I
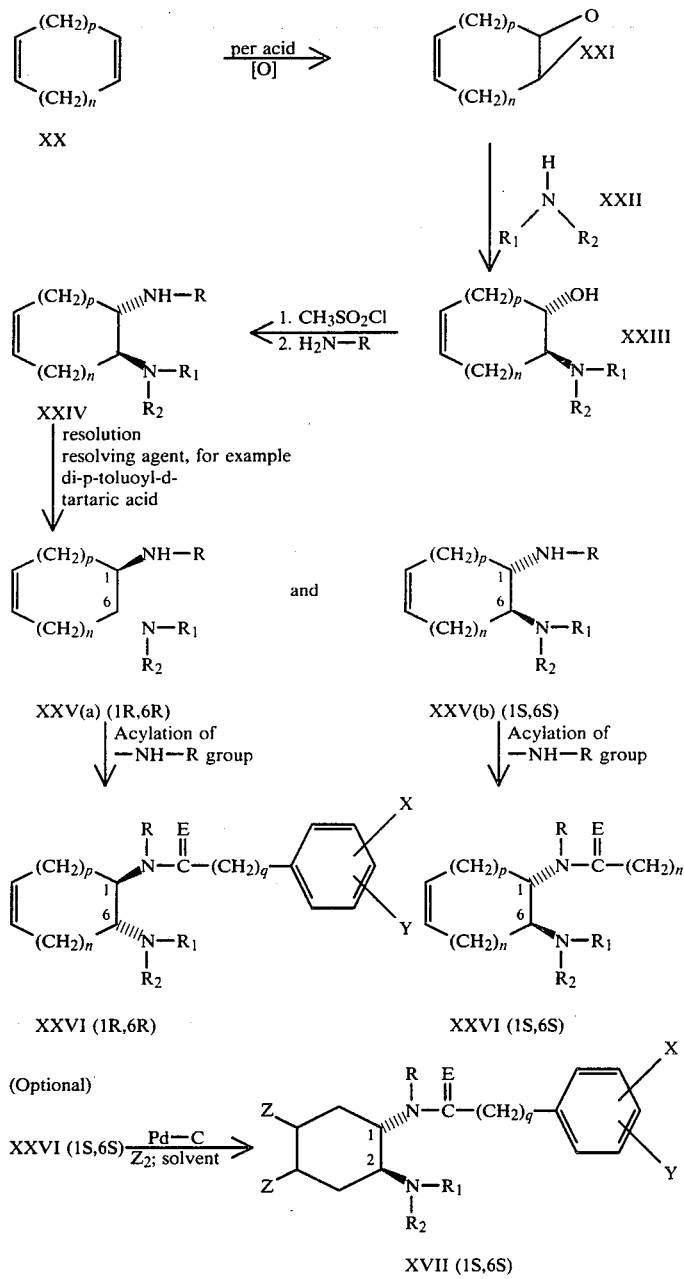
where $Z_2$ is hydrogen ($H_2$) or tritium ($T_2$).
We claim:
1. A compound of the formula
p and n are the integers 1 or 2 so that the resulting cycloalkenyl ring has from 6 to 8 ring carbons;
the wavy line (~) bond between the 6-(or 7- or 8-)position ring carbon atom and the nitrogen indicates that the bond can be either cis- or trans- with respect to the 1-substituent of the cycloalkenyl ring;
q is 0 or 1;
E is oxygen or bivalent sulfur;
X and Y are independently selected from the group consisting of hydrogen, a halogen having an atomic number of from 9 to 35; trifluoromethyl, nitro, $C_1$ to $C_3$-alkyloxy, hydroxy, azido, $C_1$ to $C_3$-alkyl, phenyl, methanesulfonyl, cyano, $-NH_2$, $C_1$ to $C_3$-alkoxycarbonyl, $C_1$ to $C_3$-alkanoyloxy, $C_1$ to $C_3$-carboxacylamino ($-NHC(O)R_4$), sulfonic acid ($-SO_3H$), $C_1$ to $C_3$-alkanoyl, ($C_2$ to $C_5$-alkenyl)C-$H_2-O-$ and benzoyl;
R is hydrogen or $C_1$ to $C_3$-alkyl;
$R_1$ and $R_2$, taken together with the nitrogen to which they are bonded complete
(a) a 1-azetidinyl or 1-pyrrolidinyl ring further unsubstituted or substituted in the 3-position of the ring with the hydroxy, $C_1$ to $C_3$-alkyl, $C_1$ to $C_3$-alkyloxy or $C_1$ to $C_3$-alkanoyloxy;
(b) a 2,5-dihydro-1H-pyrrol-1-yl ring of the formula

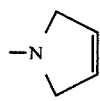

(c) a 3-azabicyclohexan-3-yl of the formula

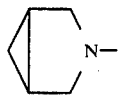

(d) a 3-azabicycloheptan-3-yl ring of the formula

(e) a 1-piperazinyl ring, further unsubstituted or substituted on the 4-position nitrogen with a $C_1$ to $C_3$-alkyl; and $R_4$ is hydrogen or $C_1$ to $C_2$-alkyl, and the acid addition salts thereof.

2. A compound according to claim 1 wherein p and n are each 1 so that the resulting cycloalkenyl ring has 6 carbon atoms, the substituent on the 6-position is trans with respect to the 1-substituent of the cycloalkenyl ring, R is $C_1$ to $C_3$-alkyl, $R_1$ and $R_2$ are taken together with the nitrogen to which they are bonded complete a 1-pyrrolidinyl or a 2,5-dihydro-1H-pyrrol-1-yl ring, E is oxygen, q is 0 or 1, and at least one of X and Y is a halogen having an atomic number of from 9 to 35, in the 3- or 4-position of the phenyl ring; and pharmacologically acceptable salts thereof.

3. A compound according to claim 1 which is 3,4-dichloro-N-methyl-N-[6-(1-pyrrolidinyl)-3-cyclohexen-1-yl]benzeneacetamide or a pharmacologically acceptable salt thereof.

4. A compound according to claim 2 which is $(1\alpha,6\beta)$-3,4-dichloro-N-methyl-N-[6-(1-pyrrolidinyl)-3-cyclohexen-1-yl]benzeneacetamide or a pharmacologically acceptable salt thereof.

5. A compound according to claim 2 which is $(1\alpha,6\beta)$-(−)-3,4-dichloro-N-methyl-N-[6-(1-pyrrolidinyl)-3-cyclohexen-1-yl]benzeneacetamide or a pharmacologically acceptable salt thereof.

6. A compound of the formula

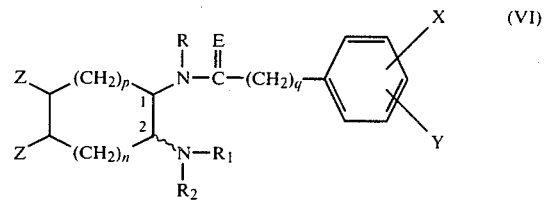

wherein
p and n are the integers 1 or 2 so that the resulting cycloalkenyl ring has from 6 to 8 ring carbons;
the wavy line ($\sim$) bond between the 2-position ring carbon atom and the nitrogen indicate that the bond can be either cis or trans with respect to the 1-substituent of the cycloalkenyl ring; the 2 groups can be cis or trans with respect to the other substituents on the cycloaliphatic ring;
each Z is tritium;
q is 0 or 1;
E is oxygen or bivalent sulfur;
X and Y are independently selected from the group consisting of hydrogen, a halogen having an atomic number of from 9 to 35; trifluoromethyl, $C_1$ to $C_3$-alkyloxy, hydroxy, $C_1$ to $C_3$-alkyl, phenyl, methanesulfonyl, $-NH_2$, $C_1$ to $C_3$-alkoxycarbonyl, $C_1$ to $C_3$-alkanoyloxy, $C_1$ to $C_3$-carboxacylamino ($-NHC(O)R_4$), sulfonic acid ($-SO_3H$), $C_1$ to $C_3$-alkanoyl, and benzoyl;
R is hydrogen or $C_1$ to $C_3$-alkyl;
$R_1$ and $R_2$, taken together with the nitrogen to which they are bonded complete:
(a) a 1-azetidinyl or 1-pyrrolidinyl ring further unsubstituted or substituted in the 3-position of the ring with hydroxy, $C_1$ to $C_3$-alkyl, $C_1$ to $C_3$-alkyloxy, or $C_1$ to $C_3$-alkanoyloxy;
(b) a 3-azabicyclohexan-3-yl ring of the formula

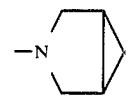

(c) a 3-azabicycloheptan-3-yl ring of the formula

(d) a 1-piperazinyl ring, further unsubstituted or substituted on the 4-position nitrogen with a $C_1$ to $C_3$-alkyl; and
$R_4$ is hydrogen or $C_1$ to $C_2$-alkyl;
and the acid addition salts thereof.

7. A compound according to claim 6 which is 3,4-dichloro-N-methyl-N-[2-(1-pyrrolidinyl)cyclohexyl-4,5-$t_2$]benzeneacetamide or a pharmacologically acceptable salt thereof.

8. A compound according to claim 6 which is $(1\alpha,2\beta)$-3,4-dichloro-N-methyl-N-[2-(1-pyrrolidinyl)-cyclohexyl-4,5-$t_2$]benzeneacetamide or a pharmacologically acceptable salt thereof.

9. A compound according to claim 6 which is (1α,2β)-(−)-3,4-dichloro-N-methyl-N-[2-(1-pyrrolidinyl)cyclohexyl-4,5-$t_2$]benzeneacetamide or a pharmacologically acceptable salt thereof.

10. A compound according to claim 1 which is N-methyl-N-[6-(1-pyrrolidinyl)-3-cyclohexen-1-yl]benzenenacetamide or a pharmacologically acceptable salt thereof.

11. A compound according to claim 1 which is (1α,6β)-N-methyl-N-[6-(1-pyrrolidinyl)-3-cyclohexen-1-yl]benzeneacetamide or a pharmacologically acceptable salt thereof.

12. A compound according to claim 1 which is (1α,6β)-(−)-N-methyl-N-[6-(1-pyrrolidinyl)-3-cyclohexen-1-yl]benzeneacetamide or a pharmacologically acceptable salt thereof.

13. A compound according to claim 6 which is N-methyl-N-[2-(1-pyrrolidinyl)cyclohexyl-4,5-$t_2$]benzeneacetamide or a pharmacologically acceptable salt thereof.

14. A compound according to claim 6 which is (1α,2β)-N-methyl-N-[2-(1-pyrrolidinyl)cyclohexyl-4,5-$t_2$]benzeneacetamide or a pharmacologically acceptable salt thereof.

15. A compound according to claim 6 which is (1α,2β)-(−)-N-methyl-N-[2-(1-pyrrolidinyl)cyclohexyl-4,5-$t_2$]benzeneacetamide or a pharmacologically acceptable salt thereof.

* * * * *

UNITED STATES PATENT OFFICE
CERTIFICATE OF CORRECTION

Patent No. 4,560,767      Dated December 24, 1985

Inventor(s) Robert A. Lahti, John M. McCall

It is certified that error appears in the above-identified patent and that said Letters Patent are hereby corrected as shown below:

Column 18, line 19: "( $\alpha,2\beta$)-(-)" should read -- ($1\alpha,2\beta$)-(-) --.

Column 19, part of formula XXV(a) should read as follows instead of as in the patent:

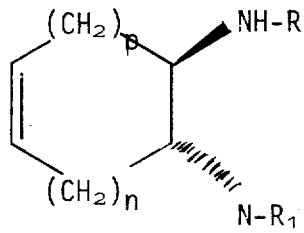

Signed and Sealed this

Twenty-ninth Day of April 1986

[SEAL]

*Attest:*

DONALD J. QUIGG

*Attesting Officer*     *Commissioner of Patents and Trademarks*